(12) United States Patent
Greenhut et al.

(10) Patent No.: US 7,904,153 B2
(45) Date of Patent: Mar. 8, 2011

(54) METHOD AND APPARATUS FOR SUBCUTANEOUS ECG VECTOR ACCEPTABILITY AND SELECTION

(75) Inventors: Saul E. Greenhut, Aurora, CO (US); Robert W. Stadler, Shoreview, MN (US); Karen J. Kleckner, New Brighton, MN (US)

(73) Assignee: Medtronic, Inc., Minneapolis, MN (US)

( * ) Notice: Subject to any disclaimer, the term of this patent is extended or adjusted under 35 U.S.C. 154(b) by 856 days.

(21) Appl. No.: 11/741,231

(22) Filed: Apr. 27, 2007

(65) Prior Publication Data

US 2008/0269813 A1 Oct. 30, 2008

(51) Int. Cl.
*A61N 1/39* (2006.01)

(52) U.S. Cl. .................... 607/5; 600/509

(58) Field of Classification Search .......... 600/509, 600/512, 508; 607/4, 5, 19, 36
See application file for complete search history.

(56) References Cited

U.S. PATENT DOCUMENTS

| | | | |
|---|---|---|---|
| 4,742,831 A | 5/1988 | Silvian et al. |
| 5,117,824 A | 6/1992 | Keimel et al. |
| 5,163,427 A | 11/1992 | Keimel |
| 5,188,105 A | 2/1993 | Keimel |
| 5,193,535 A | 3/1993 | Bardy et al. |
| 5,331,966 A | 7/1994 | Bennett et al. |
| 5,354,316 A | 10/1994 | Keimel |
| 5,545,186 A | 8/1996 | Olson et al. |
| 5,707,398 A | 1/1998 | Lu et al. |
| 5,713,367 A | 2/1998 | Arnold et al. |
| 5,752,976 A | 5/1998 | Duffin et al. |
| 5,855,593 A | 1/1999 | Olson et al. |
| 6,236,882 B1 | 5/2001 | Lee et al. |
| 6,250,309 B1 | 6/2001 | Krichen et al. |
| 6,418,346 B1 | 7/2002 | Nelson et al. |
| 6,450,172 B1 | 9/2002 | Hartlaub et al. |
| 6,480,745 B2 | 11/2002 | Nelson et al. |
| 6,496,715 B1 | 12/2002 | Lee et al. |
| 6,512,940 B1 | 1/2003 | Brabec et al. |
| 6,522,915 B1 | 2/2003 | Ceballos et al. |
| 6,622,046 B2 | 9/2003 | Fraley et al. |
| 6,782,291 B1 | 8/2004 | Bornzin et al. |
| 7,123,963 B2 | 10/2006 | Sawchuk et al. |
| 2004/0049120 A1 | 3/2004 | Cao et al. |

(Continued)

FOREIGN PATENT DOCUMENTS

EP 1774906 A 4/2007

OTHER PUBLICATIONS

International Search Report, PCT/2008/061413, Oct. 23, 2008, 7 Pages.

*Primary Examiner* — Carl H Layno
*Assistant Examiner* — Brian T Gedeon
(74) *Attorney, Agent, or Firm* — Michael C. Soldner

(57) ABSTRACT

An implantable medical device system and associated method select subcutaneous sensing electrodes for use in monitoring the heart rhythm. A subset of multiple sensing vectors is selected from a number of electrodes positioned at a first subcutaneous location and one electrode positioned at a second subcutaneous location. The subset of sensing vectors includes one vector that includes the electrode positioned at the second location. A signal quality parameter corresponding to each of the sensing vectors of the subset is determined.

21 Claims, 9 Drawing Sheets

U.S. PATENT DOCUMENTS

| | | |
|---|---|---|
| 2004/0092836 A1 | 5/2004 | Ritscher et al. |
| 2004/0220635 A1 | 11/2004 | Burnes |
| 2004/0260350 A1 | 12/2004 | Brandsetter et al. |
| 2005/0049644 A1 | 3/2005 | Warren et al. |
| 2005/0192507 A1 | 9/2005 | Warren et al. |
| 2005/0288600 A1 | 12/2005 | Zhang et al. |
| 2006/0095083 A1 | 5/2006 | Zhang et al. |
| 2007/0239220 A1 | 10/2007 | Greenhut et al. |
| 2007/0270704 A1* | 11/2007 | Ghanem et al. ............... 600/521 |

* cited by examiner

METHOD AND APPARATUS FOR SUBCUTANEOUS ECG VECTOR ACCEPTABILITY AND SELECTION

TECHNICAL FIELD

The invention relates generally to implantable medical devices, and, in particular, to a system and method for selecting ECG sensing vectors used by a subcutaneously implanted medical device.

BACKGROUND

Implantable medical devices are available for preventing or treating cardiac arrhythmias by delivering anti-tachycardia pacing therapies and electrical shock therapies for cardioverting or defibrillating the heart. Such a device, commonly known as an implantable cardioverter defibrillator or "ICD", senses a patient's heart rhythm and classifies the rhythm according to a number of rate zones in order to detect episodes of tachycardia or fibrillation.

Upon detecting an abnormal rhythm, the ICD delivers an appropriate therapy. Pathologic forms of ventricular tachycardia can often be terminated by anti-tachycardia pacing therapies. Anti-tachycardia pacing therapies are followed by high-energy shock therapy when necessary. Termination of a tachycardia by a shock therapy is commonly referred to as "cardioversion." Ventricular fibrillation (VF) is a form of tachycardia that is a serious life-threatening condition and is normally treated by immediately delivering high-energy shock therapy. Termination of VF is commonly referred to as "defibrillation." Accurate arrhythmia detection and discrimination are important in selecting the appropriate therapy for effectively treating an arrhythmia and avoiding the delivery of unnecessary cardioversion/defibrillation (CV/DF) shocks, which are painful to the patient.

In past practice, ICD systems have employed intra-cardiac electrodes carried by transvenous leads for sensing cardiac electrical signals and delivering electrical therapies. Emerging ICD systems are adapted for subcutaneous or submuscular implantation and employ electrodes incorporated on the ICD housing and/or carried by subcutaneous or submuscular leads. These systems, referred to generally herein as "subcutaneous ICD" or "SubQ ICD" systems, do not rely on electrodes implanted in direct contact with the heart. SubQ ICD systems are less invasive and are therefore implanted more easily and quickly than ICD systems that employ intra-cardiac electrodes. However, greater challenges exist in reliably detecting cardiac arrhythmias using a subcutaneous system. The R-wave amplitude on a SubQ ECG signal may be on the order of one-tenth to one-one hundredth of the amplitude of intra-ventricular sensed R-waves. Furthermore, the signal quality of subcutaneously sensed ECG signals are likely to be more affected by myopotential noise, environmental noise, patient posture and patient activity than intra-cardiac myocardial electrogram (EGM) signals. As such, systems and methods that promote reliable and accurate detection of arrhythmias using ECG signals sensed by subcutaneous electrodes are needed.

BRIEF DESCRIPTION OF THE DRAWINGS

Aspects and features of the present invention will be appreciated as the same becomes better understood by reference to the following detailed description of the embodiments of the invention when considered in connection with the accompanying drawings, wherein.

DETAILED DESCRIPTION

Figure 1:
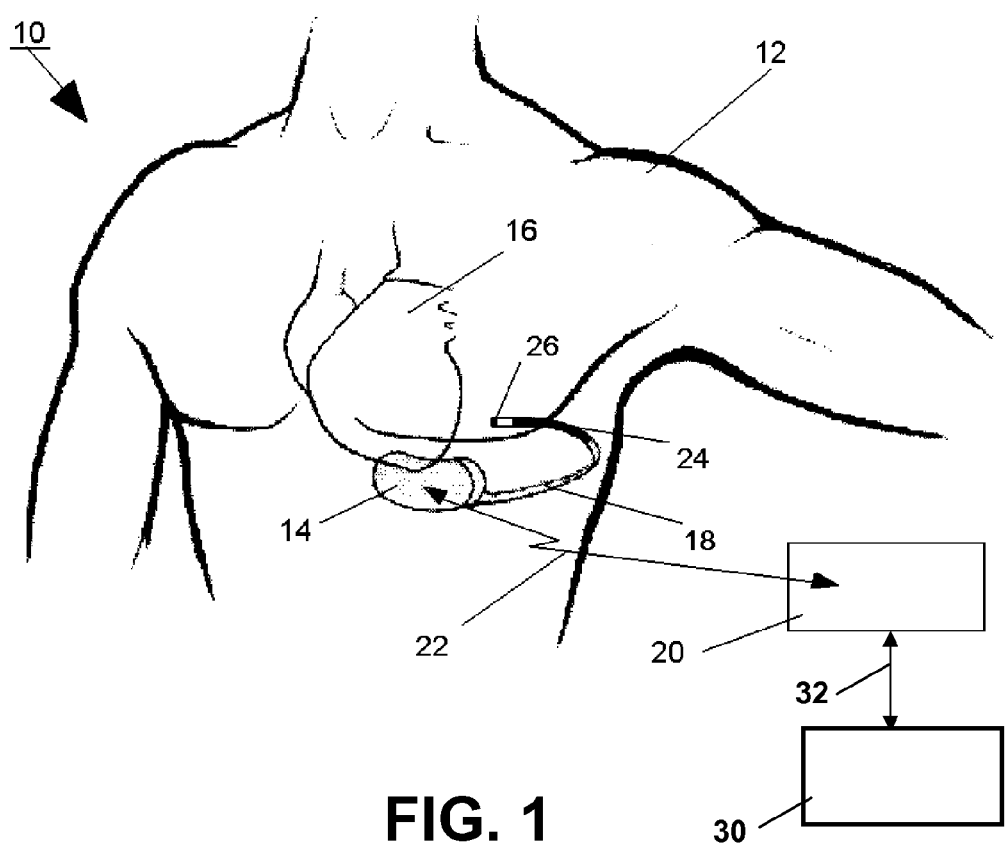
FIG. 1 depicts one example of a SubQ ICD in which the present invention may be embodied.

In the following description, references are made to illustrative embodiments for carrying out the invention. It is understood that other embodiments may be utilized without departing from the scope of the invention. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

The invention is directed toward a subcutaneously implantable medical device system and associated method for monitoring the ECG signals for detecting arrhythmias. The term "subcutaneous" as used herein with regard to electrodes and leads generally refers to any electrode or lead that is adapted for implantation in a subcutaneous, submuscular, or any other internal body location that is not in direct contact with the heart. As such, subcutaneous ECG signals are signals sensed using electrodes that are not in or on the heart. The sensed ECG signals, which can also be referred to as "far-field signals," are generally used by the device for accumulating diagnostic data and/or for detecting the need for delivering a therapy. If the signal quality is below an acceptable level, the usefulness of the signals for diagnostic purposes will be limited.

Furthermore, the low quality signals may be unreliable in detecting a need for delivering a therapy.

FIG. 1 depicts one example of a SubQ ICD 14 in which the present invention may be embodied. SubQ ICD 14 is implanted subcutaneously in a patient 12, outside the ribcage and anterior to the cardiac notch. A subcutaneous lead 18 carrying a sensing electrode 26 and a high-voltage, cardioversion defibrillation coil electrode 24, is electrically coupled at its proximal end to SubQ ICD 14. The distal end of lead 18 is tunneled subcutaneously into a posterior location adjacent to a portion of the latissimus dorsi muscle of patient 12. Specifically, lead 18 is tunneled subcutaneously from the median implant pocket of SubQ ICD 14 laterally and posterially to the patient's back to a location opposite the heart such that the heart 16 is generally disposed between the anteriorly positioned SubQ ICD 14 and the posteriorly positioned distal electrode coil 24 and distal sensing electrode 26.

An external device 20 is shown in telemetric communication with SubQ ICD 14 by RF communication link 22. External device 20 may be a programmer, home monitor, hand-held or other device adapted to communicate with SubQ ICD 14. Communication link 22 may be any appropriate RF link, including Bluetooth, WiFi, and MICS.

External device 20 may be Internet enabled or coupled to a communication network 32 to allow communication between external device 20 and a networked device 30. Networked device 30 may be a Web-based centralized patient management database, a computer, a cell phone or other hand-held device. Networked device 30 communicates with external device 20 via communications network 32, which may be an Internet connection, a local area network, a wide area network, a land line or satellite based telephone network, or cable network. Networked device 30 may be used to remotely monitor and program SubQ ICD 14 via external device 20. Systems and methods for remotely communicating with an implantable medical device are generally disclosed in U.S. Pat. No. 5,752,976 (Duffin et al.), U.S. Pat. No. 6,480,745 (Nelson et al.), and U.S. Pat. No. 6,418,346 to (Nelson et al.), and U.S. Pat. No. 6,250,309 (Krichen et al.).

Figure 2:
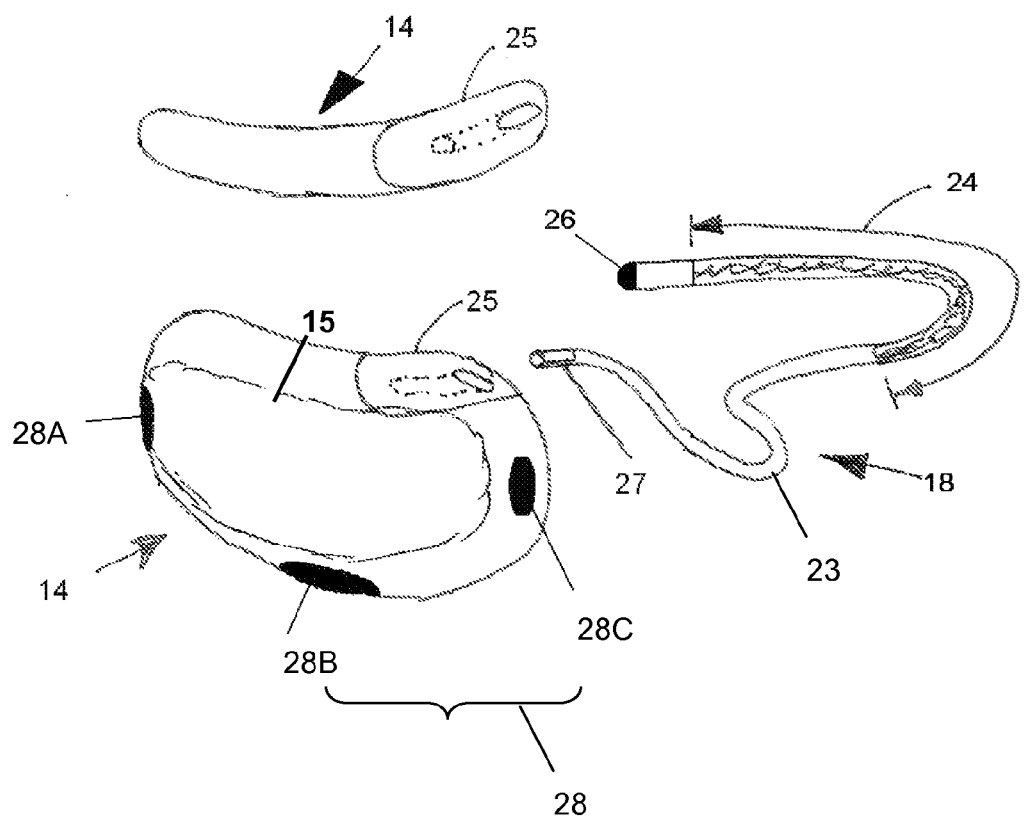
FIG. 2 is a top and plan view of the SubQ ICD shown in FIG. 1.

FIG. 2 is a top and plan view of SubQ ICD 14. SubQ ICD 14 includes a generally ovoid housing 15 having a substantially kidney-shaped profile. The plan view shows the generally ovoid construction of housing 15 that promotes ease of subcutaneous implant. This structure is ergonomically adapted to minimize patient discomfort during normal body movement and flexing of the thoracic musculature. Connector block 25 is coupled to housing 15 for receiving the connector assembly 27 of subcutaneous lead 18. SubQ ICD housing 15 may be constructed of stainless steel, titanium or ceramic. Electronics circuitry enclosed in housing 15 of SubQ ICD 14 may be implemented on a polyamide flex circuit, printed circuit board (PCB) or ceramic substrate with integrated circuits packaged in leadless chip carriers and/or chip scale packaging (CSP).

Subcutaneous lead 18 includes distal coil electrode 24, distal sensing electrode 26, an insulated flexible lead body 23 and a proximal connector assembly 27 adapted for connection to SubQ ICD 14 via SubQ ICD connector block 25. Distal sensing electrode 26 is sized appropriately to match the sensing impedance of a housing-based subcutaneous electrode array (SEA) 28. SEA 28 includes a plurality of electrodes 28A, 28B, and 28C mounted on the housing 15. Three electrodes 28A, 28B, and 28C positioned in an orthogonal arrangement are included in SEA 28 in the embodiment shown in FIG. 2. Other embodiments of a SubQ ICD may include any number of electrodes mounted on or incorporated in housing 15. It is recognized that any combination of lead-based and/or housing based electrodes may be used for sensing subcutaneous ECG signals. Multiple subcutaneous electrodes are provided to allow multiple subcutaneous ECG sensing vector configurations.

Electrode assemblies included in SEA 28 are welded into place on the flattened periphery of the housing of SubQ ICD 14. The complete periphery of the SubQ ICD may be manufactured to have a slightly flattened perspective with rounded edges to accommodate the placement of SEA assemblies. The SEA electrode assemblies are welded to SubQ ICD housing 15 (in a manner that preserves hermaticity of the housing 15) and are connected via wires (not shown in FIG. 2) to internal electronic circuitry (described herein below) inside housing 15. SEA electrode assemblies may be constructed of flat plates, or alternatively, spiral electrodes as described in U.S. Pat. No. 6,512,940 (Brabec, et al). SEA electrode assembly are mounted in a non-conductive surround shroud, for example as generally described in U.S. Pat. No. 6,522,915 (Ceballos, et al.) or in U.S. Pat. No. 6,622,046 (Fraley, et al.). The '940, '915 and '046 patents are hereby incorporated herein by reference in their entireties.

Figure 3:
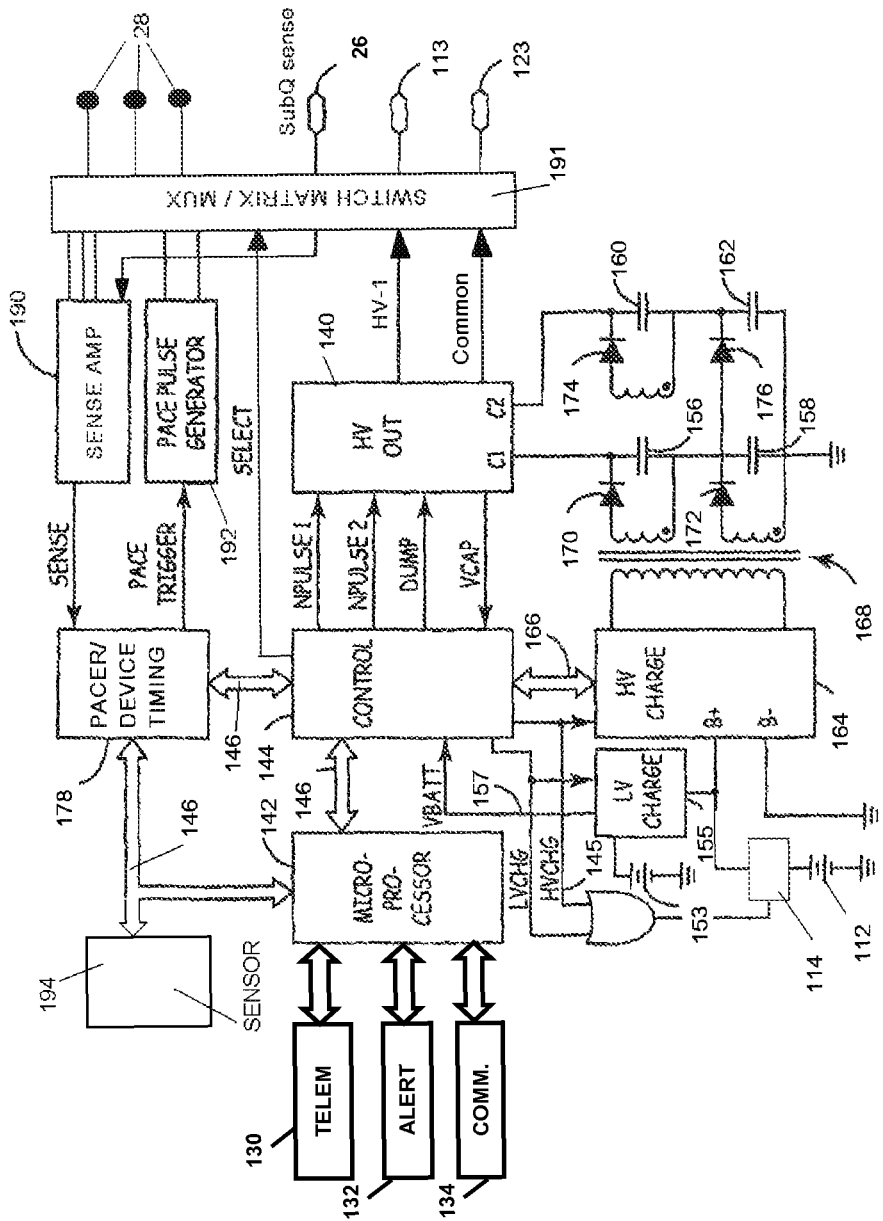
FIG. 3 is a functional block diagram of the SubQ ICD.

The electronic circuitry employed in SubQ ICD 14 is configured for detecting tachycardias using the sensed ECG and provide cardioversion/defibrillation shocks in response to detected VT/VF as well as post-shock pacing as needed while the heart recovers. A simplified block diagram of such circuitry adapted to function employing subcutaneous sensing and cardioversion/defibrillation electrodes as described herein is shown in FIG. 3. It will be understood by a skilled artisan that the simplified block diagram of FIG. 3 does not show all of the conventional components and circuitry included in an ICD such as digital clocks and clock lines power supply lines for powering the circuits and providing pacing pulses.

FIG. 3 is a functional block diagram of SubQ ICD 14. SubQ ICD 14 functions are controlled by software, firmware and hardware that cooperatively operate to monitor the ECG signals, determine when a CV/DF shock or pacing is necessary, and deliver prescribed CV/DF and pacing therapies. The particular architecture of SubQ ICD 14 for controlling and executing device functions may include application specific integrated circuit (ASIC), an electronic circuit, a processor (shared, dedicated, or group) and memory that execute one or more software or firmware programs, a combinational logic circuit, or other suitable components or combinations of components that provide the described functionality.

Such functionality includes delivering single phase, simultaneous biphasic, or sequential biphasic CV/DF shocks using the SubQ ICD housing 15 (shown in FIG. 2) coupled to the COMMON output 123 of high voltage output circuit 140 and CV/DF electrode 24 (shown in FIG. 1) coupled to the HV output terminal 113. Circuitry for delivering CV/DF shocks may generally correspond to circuitry set forth in commonly assigned U.S. Pat. No. 5,163,427 (Keimel) and U.S. Pat. No. 5,188,105 (Keimel).

The CV/DF shock energy and capacitor charge voltages provided by SubQ ICD 14 are generally intermediate to those supplied by ICDs having at least one CV/DF electrode in contact with the heart and most automatic external defibrillators (AEDs) having CV/DF electrodes in contact with the skin. The typical maximum voltage necessary for ICDs employing an intra-cardiac electrode delivering most biphasic waveforms is approximately 750 Volts with an associated maximum energy of approximately 40 Joules. The typical maximum voltage necessary for defibrillation by AEDs is approximately 2000-5000 Volts with an associated maximum energy of approximately 200-360 Joules depending upon the model and waveform used. A SubQ ICD will use maximum CV/DF voltages in the range of about 700 to about 3150 Volts, associated with energies of about 25 Joules to about 210 Joules. The total high voltage capacitance could range from about 50 to about 300 microfarads. Such CV/DF shocks are only delivered when a malignant tachyarrhythmia, e.g., ventricular fibrillation, is detected through processing of the subcutaneous cardiac ECG signals.

In FIG. 3, sense amp 190 in conjunction with pacer/device timing circuit 178 processes the subcutaneous ECG sense signals received from sensing vectors selected from SEA 28 (FIG. 2) and sensing electrode 26. In one embodiment, two ECG sensing vectors are selected from the six possible vectors between the three electrodes included in SEA 28 and the lead-based sensing electrode 26. The selection of the sensing electrode pairs is made through the switch matrix/multiplexer 191 in a manner to provide the most reliable R-wave sensing and arrhythmia detection of the ECG signal according to methods described herein. The subcutaneous ECG signals are passed through the switch matrix/multiplexer 191 to the input of the sense amplifier 190 that, in conjunction with pacer/device timing circuit 178, evaluates the sensed ECG signals. Signal processing methods that may be implemented in sense amplifier 190 and pacer/device timing circuit 178 will be described in greater detail below. Sensing subcutaneous ECG signals in the presence of noise may be aided by the use of appropriate denial and extensible accommodation periods as generally described in U.S. Pat. No. 6,236,882 (Lee, et al.).

Bradycardia or asystole is typically determined by expiration of an escape interval timer within the pacer timing circuit 178 and/or the control circuit 144. Pace trigger signals are applied to the pacing pulse generator 192 causing generation of pacing pulses when the escape interval expires (the interval between successive R-waves exceeds the escape interval). Bradycardia pacing is often temporarily provided to maintain cardiac output during recovery from a CV/DF shock. Pace pulse generator 192 provides pacing pulses that are higher voltage pulses compared to pacing pulses delivered by intracardiac electrodes. Low voltage power supply 153 provides power to circuitry included in SubQ ICD 14 and for generating low voltage pacing pulses. Pace pulse generator 192 may alternatively be incorporated in the HV output circuitry 140 for delivering pacing pulses of adequate energy for capturing the heart using subcutaneous electrodes.

Detection of a malignant tachyarrhythmia is determined in the control circuit 144 as a function of the intervals between R-wave sense event signals determined from one or more of the selected ECG signals. The R-wave sense event signals are output from the pacer/device timing 178 and sense amplifier circuit 190 to the timing and control circuit 144. It should be noted that implemented arrhythmia detection algorithms may utilize not only interval based signal analysis methods but also supplemental sensors and morphology processing methods and apparatus.

Supplemental sensors 194, such as tissue color, tissue oxygenation, respiration, patient activity and the like, may be used to contribute to the decision to apply or withhold a defibrillation therapy. Certain steps in the performance of the arrhythmia detection algorithm criteria are cooperatively performed in microcomputer 142, including microprocessor, RAM and ROM, associated circuitry, and stored detection criteria that may be programmed into RAM via a telemetry interface 130.

Data and commands are exchanged between microcomputer 142 and timing and control circuit 144, pacer/device timing circuit 178, and high voltage output circuit 140 via a bidirectional data/control bus 146. The pacer/device timing circuit 178 and the control circuit 144 are clocked at a slow clock rate. The microcomputer 142 is normally asleep, but is awakened and operated by a fast clock by interrupts developed by each R-wave sense event, on receipt of a downlink telemetry programming instruction or upon delivery of cardiac pacing pulses to perform any necessary mathematical calculations, to perform tachycardia and fibrillation detection procedures, and to update the time intervals monitored and controlled by the timers in pacer/device timing circuitry 178.

The algorithms and functions of the microcomputer 142 and control circuit 144 employed and performed in detection of tachyarrhythmias may correspond to those generally disclosed in commonly assigned U.S. Pat. No. 5,354,316 (Keimel); U.S. Pat. No. 5,545,186 (Olson, et al.), U.S. Pat. No. 5,855,593 (Olson, et al.); and U.S. Pat. No. 5,193,535 (Bardy, et al.), all of which patents are hereby incorporated herein by reference in their entireties. Particular algorithms for detection of ventricular fibrillation and malignant ventricular tachycardias can be selected from among the comprehensive algorithms for distinguishing atrial and ventricular tachyarrhythmias from one another and from high rate sinus rhythms as set forth, for example, in the '316, '186, '593 and '593 patents.

The detection algorithms are highly sensitive and specific for the presence or absence of life threatening ventricular arrhythmias, e.g., ventricular tachycardia (VT) and ventricular fibrillation (VF). Operational circuitry may detect the presence of atrial fibrillation (A FIB). A-FIB detection can include using R-R cycle length instability detection algorithms, for example as generally disclosed in U.S. Pat. Publication No. 2004/0092836 (Ritscher et al.). If A-FIB has been detected, the operational circuitry may provide QRS synchronized atrial CV/DF using a similar range of shock energy and wave shapes used for ventricular CV/DF.

Operating modes and parameters of the detection algorithm are programmable. The detection algorithm is particularly focused on the detection of VF and high rate VT (for example rates greater than 170 bpm). As part of the detection algorithm's applicability to children, the upper rate range is programmable upward for use in children, known to have rapid supraventricular tachycardias and more rapid VF.

When a malignant tachycardia is detected, high voltage capacitors 156, 158, 160, and 162 are charged to a pre-programmed voltage level by a high-voltage charging circuit 164 with charging current from high voltage battery 112 connected through switch 114. It is generally considered inefficient to maintain a constant charge on the high voltage output capacitors 156, 158, 160, 162. Instead, charging is initiated when control circuit 144 issues a high voltage charge command HVCHG delivered on line 145 to high voltage charge circuit 164 and charging is controlled by means of bidirectional control/data bus 166 and a feedback signal VCAP from the HV output circuit 140. High voltage output capacitors 156, 158, 160 and 162 typically correspond to flat, aluminum electrolytic or wet tantalum construction.

High voltage output capacitors 156, 158, 160, and 162 may be charged to very high voltages, e.g., 700-3150V, to be discharged through the body and heart between the subcutaneous electrode coupled to HV output terminal 113 and COMMON 123. High voltage capacitors 156, 158, 160 and 162 are charged by high voltage charge circuit 164 and a high frequency, high-voltage transformer 168. Proper charging polarities are maintained by diodes 170, 172, 174 and 176 interconnecting the output windings of high-voltage transformer 168 and the capacitors 156, 158, 160, and 162. Timing and control circuit 144 terminates the high voltage charge command HVCHG when the VCAP signal matches the programmed capacitor output voltage, i.e., the CV/DF peak shock voltage.

Control circuit 144 then develops first and second control signals NPULSE 1 and NPULSE 2, respectively, that are applied to the high voltage output circuit 140 for triggering the delivery of cardioverting or defibrillating shocks. In particular, the NPULSE 1 signal triggers discharge of the first capacitor bank, comprising capacitors 156 and 158. The NPULSE 2 signal triggers discharge of the first capacitor bank and a second capacitor bank, comprising capacitors 160 and 162. It is possible to select between a plurality of output pulse regimes simply by modifying the number and time order of assertion of the NPULSE 1 and NPULSE 2 signals. The NPULSE 1 signals and NPULSE 2 signals may be provided sequentially, simultaneously or individually. In this way, control circuitry 144 serves to control operation of the high voltage output stage 140, which delivers high energy CV/DF shocks between the pair of the CV/DF electrodes coupled to the HV-1 terminal 113 and COMMON terminal 123 as shown in FIG. 3. The SubQ ICD 14 can be programmed to attempt to deliver cardioversion shocks to the heart in timed synchrony with a detected R-wave. Episode data related to the detection of the tachyarrhythmia and delivery of the CV/DF shock can be stored in RAM for uplink telemetry transmission to an external programmer as is well known in the art to facilitate in diagnosis of the patient's cardiac state.

SubQ ICD 14 includes telemetry circuit 130 so that it is capable of being programmed by means of external programmer 20 via a bidirectional telemetry link 22 (shown in FIG. 1). Uplink telemetry allows device status and diagnostic/event data to be sent to an external device 20 for review by the patient's physician. Downlink telemetry allows the external programmer via physician control to allow the programming of device function and the optimization of the detection and therapy for a specific patient.

Programmers typically communicate with an implanted device via a bi-directional radio-frequency telemetry link, so that the programmer can transmit control commands and operational parameter values to be received by the implanted device, and so that the implanted device can communicate diagnostic and operational data to the programmer.

SubQ ICD 14 may further include patient alert circuitry 132. Patient alert circuitry 132 delivers a sensory signal perceivable by the patient for notifying the patient of particular events or conditions detected by SubQ ICD 14. Patient alert circuitry 132 may be provided for broadcasting sounds audible by the patient, delivering stimulation pulses to the thoracic musculature in the region of SubQ ICD 14 or lead 18 using any available electrodes, or causing SubQ ICD 14 to vibrate. Patient alert circuitry may correspond to the audible patient alert generally disclosed in U.S. Pat. No. 6,450,172 (Hartlaub et al) for example.

SubQ ICD 14 may further include a communications unit 134 for allowing wireless communication directly between SubQ ICD 14 and a wireless communication networked device 30 (shown in FIG. 1), such as a cell phone, hand-held device, or computer using WiFi, Bluetooth, or other wireless RF connection.

Figure 4:
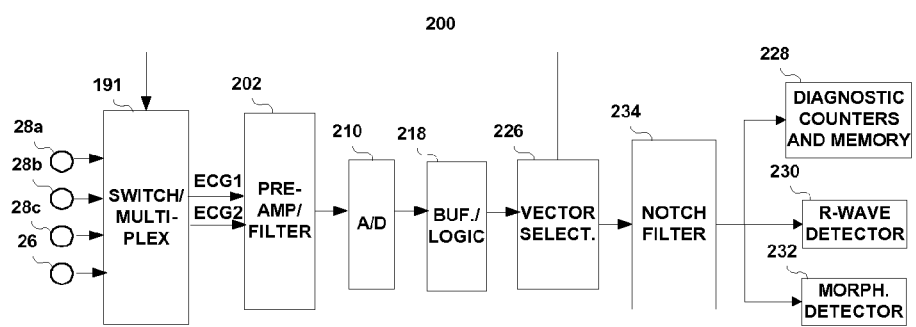
FIG. 4 shows a functional block diagram summarizing signal processing methods performed by the SubQ ICD.

FIG. 4 shows a block diagram 200 summarizing signal processing methods performed by the SubQ ICD 14. Subcutaneous ECG signals sensed between sensing vectors defined by each paired combination of the three electrodes included in SEA 28 and the lead based sensing electrode 26 are selected through switch/multiplexer 191. In the embodiment shown, two ECG signals, ECG1 and ECG2, out of six possible ECG signals are selected from SEA 28 and sensing electrode 26 by switch/multiplexer 191. The selected signals are amplified and bandpass filtered (e.g. 2.5-105 Hz) by preamplifier 202. Pre-amplifier 202 is included in sense amplifier circuitry 190 (shown in FIG. 3).

The amplified and filtered signals are directed to A/D converter 210 which operates to sample the time varying analog ECG signals to provide a digitized ECG signal to temporary buffers/control logic 218. Temporary buffers/control logic 218 shifts the digital data through stages in a FIFO manner under the control of pacer/device timing circuit 178 (FIG. 3). Vector selection block 226 operates to identify the two out of six ECG sensing vectors having optimal signal quality for sensing cardiac signals as will be described herein. In one embodiment, ECG sensing vectors are selected two at a time by switch/multiplexer 191 for evaluation by vector selection module 226. It is recognized that in alternative embodiments one or more ECG sensing vectors may be selected simultaneously or sequentially for evaluation by vector selection module 226.

Automatic methods for performing vector selection at module 226 will be described in detail herein. ECG sensing vector selection may alternatively be determined by the patient's physician and programmed via telemetry link 22 from external device 20, in particular when the automatic vector selection does not find at least two acceptable ECG sensing vectors.

In order to automatically select the ECG sensing vectors, the ECG signal quality is evaluated by determining vector selection metrics for each sensing vector. "Signal quality" refers to the reliability of the signal in accurately detecting and discriminating heart rhythms according to implemented sensing and detection/discrimination algorithms. In particular, the signal quality may relate to the reliability of the signal in providing accurate heart rate estimation and/or accurate morphological waveform separation for distinguishing between the patient's usual sinus rhythm and tachyarrhythmias. Determining ECG signal quality may include determining a signal amplitude such as an R-wave amplitude, a signal-to-noise ratio such as an R-wave peak amplitude to a maximum or average waveform amplitude between R-waves or an R-wave to T-wave amplitude ratio, a signal slope or slew rate, a low slope content, a relative high versus low frequency power, mean frequency or spectral width estimation, probability density function, normalized mean rectified amplitude, or any combination of these parameters or other signal quality parameters.

Automatic vector selection might be done at implantation and again on a periodic basis (daily, weekly, monthly) or both. At implant, automatic vector selection may be initiated as part of an automatic device turn-on procedure that performs such activities as measuring lead impedances and battery voltages. The device turn-on procedure may be initiated by the implanting physician (e.g., by pressing a programmer button) or, alternatively, may be initiated automatically upon automatic detection of device/lead implantation. The turn-on procedure may also use the automatic vector selection criteria to determine if ECG signal quality is adequate for the current patient and for the device and lead position, prior to suturing SubQ ICD 14 in place and closing the subcutaneous pocket incision. Knowledge of an ECG signal quality measurement would allow the implanting physician to maneuver the device and/or lead to a new location or orientation to improve the quality of the ECG signals as required. The preferred vectors might be those vectors with the indices that maximize rate estimation and detection accuracy. There may also be an a priori set of vectors that are preferred by the physician, and as long as those vectors exceed some minimum selection threshold criteria, the a priori preferred vectors are chosen.

Depending upon power consumption of the automatic vector acceptability/selection feature, power requirements of the device, and vector-to-vector variability, signal quality parameters may be measured for all available vectors (or alternatively, a subset) as often as desired to ensure for optimal ECG sensing using the sensing vectors having the greatest or at least acceptable signal quality. Data may be gathered, for example, on a minute, hourly, daily, weekly or monthly basis. More frequent measurements (e.g., every minute) may be averaged over time and used to select vectors based upon susceptibility of vectors to occasional noise, motion noise, or EMI, for example.

Alternatively, the SubQ ICD 14 may have an indicator/sensor of patient activity (piezo-resistive, accelerometer, impedance, or the like) and delay automatic signal quality measurements during periods of moderate or high patient activity to periods of minimal to no activity. One representative scenario may include testing/evaluating ECG vectors once daily or weekly while the patient has been determined to be asleep, e.g., using an internal clock (e.g., 2:00 am) or, alternatively, infer sleep by determining the patient's position (via a 2- or 3-axis accelerometer) and a lack of activity.

If infrequent automatic, periodic measurements are made, it may also be desirable to measure noise (e.g., muscle, motion, EMI, etc.) in the signal and postpone the vector signal quality parameter until after the noise has subsided.

SubQ ICD 14 may optionally have an indicator of the patient's posture (via a 2- or 3-axis accelerometer). This sensor may be used to ensure that the differences in ECG quality are not simply a result of changing posture/position. The sensor may be used to gather data in a number of postures so that ECG quality may be averaged over these postures or, alternatively, selected for a preferred posture. For example, there might be a learning period to identify the preferred vectors for a given posture which would be selected when the patient assumes that posture.

Continuing with FIG. 4, the ECG signals received from the selected sensing vectors may be passed through a notch filter 234 to a diagnostic module 228. Diagnostic module 228 compresses the digital ECG data, and stores the data in memory or provides the data for uplink telemetry for review by a clinician. The stored data is available for diagnostic functions such as storing detected arrhythmia episodes, or providing data for various event counters or other diagnostic features used to monitor the patient and/or evaluate device function such as an asystole counter, a bradycardia counter, and a minimum sensing threshold counter.

The selected ECG signals are additionally used to provide R-wave interval sensing via R-wave detection block 230. R-wave detection block 230 may include additional filtering of the selected ECG signals and includes a rectifier and auto-threshold block for performing R-wave event detection. Reference is made, for example, to U.S. Pat. No. 5,117,824 (Keimel, et al); U.S. Publication No. 2004/0049120, (Cao, et al.), and U.S. Publication No. 2004/0260350 (Brandstetter, et al.). The heart rate estimation may be determined from a predetermined number of consecutive R-R intervals, for example by determining a running mean, median, or minimum interval or other estimation determined from the most recently sensed intervals. The oldest heart rate estimation value is removed as a new data value is added.

The selected ECG signals may be applied to ECG morphology detector 232. Morphology detector 232 may include additional filtering and performs signal morphology evaluation that may be used for subsequent rhythm detection/determination. While particular signal processing blocks are shown in FIG. 4, it is recognized that alternative signal processing circuitry and methods may be implemented for sensing subcutaneous ECG signals and processing sensed signals for use in detecting cardiac arrhythmias.

Figure 5:
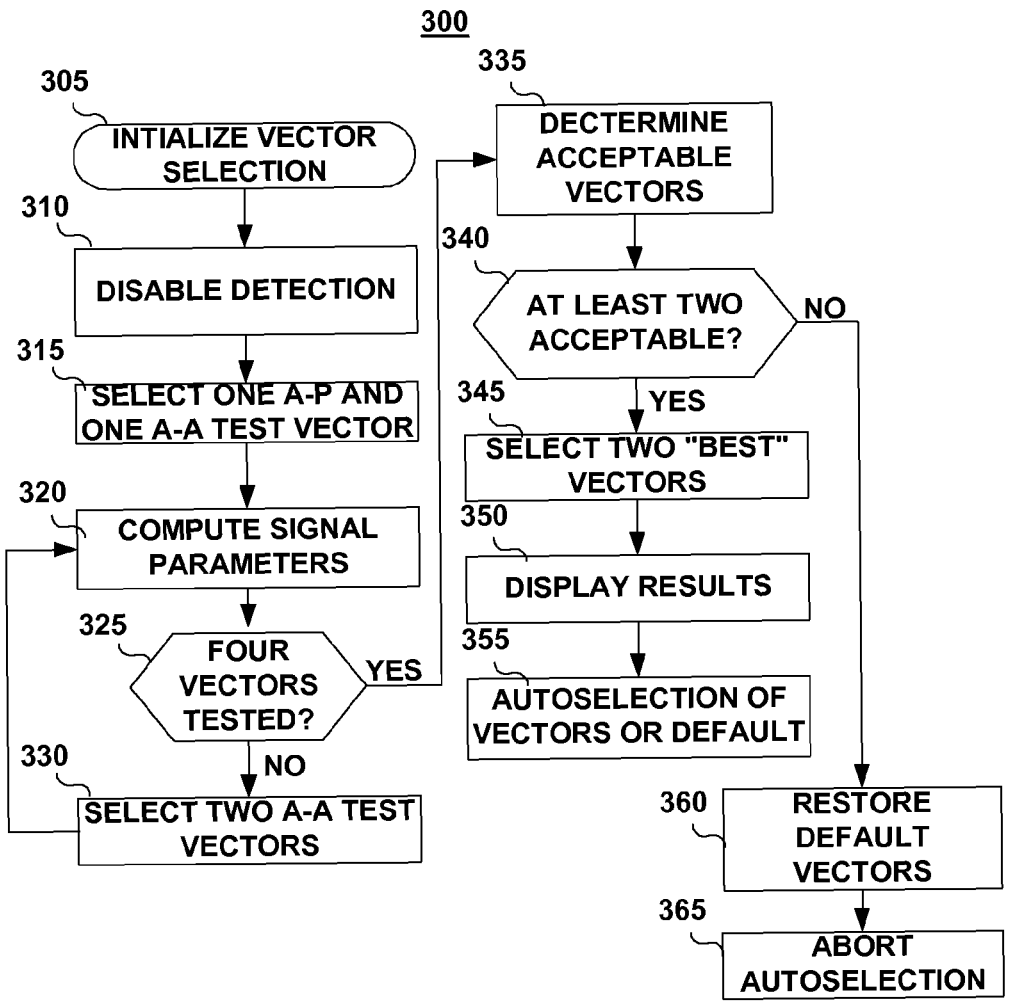
FIG. 5 is a flow chart of one method for selecting ECG sensing vectors for use in a SubQ ICD or other device relying on subcutaneous ECG signal sensing.

FIG. 5 is a flow chart of one method for selecting ECG sensing vectors for use in a SubQ ICD or other device relying on subcutaneous ECG signal sensing. Flow chart 300 is intended to illustrate the functional operation of the device, and should not be construed as reflective of a specific form of software or hardware necessary to practice the invention. It is believed that the particular form of software will be determined primarily by the particular system architecture employed in the device and by the particular detection and therapy delivery methodologies employed by the device. Providing software to accomplish the present invention in the context of any modern implantable electronic device, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 305, vector selection is initialized. Initialization may be performed manually by a clinician during an implant procedure or during a patient follow-up. Initialization may alternatively occur automatically on a periodic basis or upon automatic detection of device/lead implantation or in response to monitoring signal quality parameters. At block 310, arrhythmia detection is disabled to avoid inappropriate arrhythmia detection during vector testing, otherwise a sensing vector that is selected for testing and is ultimately determined to be an unacceptable vector may inadvertently result in an arrhythmia detection during the vector selection process. Alternatively, heart rate estimation may continue with a single, non-changing vector on one ECG sensing channel, while the second ECG channel is rotated through the other possible vector signals for testing. If the fixed channel detects a high rate during this period of vector acceptability/selection testing, the vector testing can be postponed until after the high rate episode is classified.

At block 315, two vectors are initially selected for testing. In one embodiment, one anterior-posterior (A-P) vector is selected using a posteriorly positioned sensing electrode and one anteriorly positioned sensing electrode. In the embodiment shown in FIG. 1, the posterior sensing electrode 26 included on the subcutaneous lead 18 is selected with any of the electrodes 28A, 28B, and 28C in SEA 28 (shown in FIG. 2). A second anterior-anterior (A-A) vector is selected using any two anteriorly positioned sensing electrodes. With reference to FIG. 2, any two of the three electrodes 28A, 28B, and 28C in SEA 28 are selected. The two electrodes selected for the A-A vector may or may not include the same anterior electrode used in the A-P vector selected.

At block 320, signal parameters are computed which will be used to determine if the test sensing vectors have an acceptable signal quality for use in reliably monitoring the patient's heart rhythm. The computed signal parameters and corresponding vector identification may be transferred to an external device for display to the clinician during or after execution of method 300. One or more signal parameters may be computed for each vector and such parameters may include, for example, any of: an R-wave amplitude, a signal-to-noise ratio such as an R-wave peak amplitude to a maximum or average waveform amplitude between R-waves or an R-wave to T-wave amplitude ratio, a signal slope or slew rate, a low slope content, a relative high versus low frequency power, mean frequency or spectral width estimation, probability density function, normalized mean rectified amplitude, or any combination of these metrics or other signal quality parameters useful in evaluating the quality of the ECG signal for heart rhythm monitoring, which will depend on the particular arrhythmia detection methods used.

In one embodiment, the R-wave amplitude and the low slope content parameter are computed for each test vector. The signal parameters computed at block 320 are computed for one or more cardiac cycles or for one or more intervals of time for each vector. When measurements are made over multiple cardiac cycles or measurement time intervals, the signal parameter may be derived as a minimum, maximum, median, average or other representative value of the given signal characteristic measured for multiple cardiac cycles or measurement intervals. For example, in one embodiment six consecutive R-wave amplitudes are measured for each vector and the nth smallest R-wave amplitude, for example the fourth smallest R-wave amplitude, is stored for each vector as an R-wave amplitude parameter. It is recognized that numerous variations may be conceived by one having skill in the art and the benefit of the teachings provided herein for defining signal quality parameters that are computed from test vector signals for use in ECG vector selection.

The low slope content is approximated as the ratio of the number of data points less than a low slope threshold to the total number of data points determined from an ECG vector signal during a predetermined signal segment, for example a three second segment. In one embodiment, the slope data points are acquired by approximating the slope between ECG signal sample points as the sample-to-sample difference of the filtered ECG signal. The low slope threshold is based on the slope content of the signal segment. For example, the low slope threshold may be defined as a percentage, for example 10%, of the largest absolute slope determined from the signal segment. The low slope content is then determined as the number of slope data points having an absolute value less than the low slope threshold to the total number of slope data points occurring in the signal segment. The low slope content of non-shockable tachycardias is typically high relative to the low slope content of shockable tachycardias. As such, the low slope content is a useful ECG signal parameter to monitor for determining when tachycardia therapies are needed. As used herein, the term "shockable rhythm" refers to malignant or life threatening ventricular tachyarrhythmias, which can be terminated by cardioversion/defibrillation (CV/DF) shock delivery. "Non-shockable" refers to non-malignant heart rhythms that are not life threatening. In one embodiment, low slope content values are determined for three or more three-second ECG segments for each test vector. The median of the low slope content is stored for each test vector.

It is recognized that if method 300 is unable to derive the required number of signal measurements, e.g. six R-wave amplitudes and three LSC values, required to compute the signal quality parameters for each test vector, the automatic vector selection method can be aborted. If at least four vectors have not yet been tested, as determined at decision block 325, method 300 proceeds to block 330 to select two new test vectors. In one embodiment, the two new test vectors are A-A test vectors such that at least one A-P vector and all three A-A vectors are tested. Referring to the embodiment shown in FIG. 2, the remaining two vectors available between the three SEA electrodes 28A, 28B, and 28C are selected. The signal parameters are computed for the newly selected test vectors at block 320.

Once the four vectors have been tested, method 300 proceeds to block 335 to determine if the tested vectors are acceptable. Methods for determining if a vector is acceptable or unacceptable will be further described below. If at least two of the four tested vectors are acceptable, as determined at decision block 340, the two "best" vectors are selected at block 345 based on the signal quality parameters used for determining acceptability. All test results, including the recommended "best" sensing vectors, may be transmitted to an external device for display to a clinician at block 350. At block 355, the SubQ ICD may automatically select the "best" sensing vectors for processing by the SubQ ICD for heart rhythm detection. Alternatively, the default or originally programmed vector selections may be restored allowing a clinician to manually program the vector selections having knowledge of the testing results.

If at least two vectors out of the four tested vectors are not acceptable, at block 340, the originally programmed or default vectors are restored at block 360, and the automatic vector selection process is aborted at block 365. A message may be transmitted to an external device and displayed to notify the clinician of the results or a patient alert signal may be generated.

It is recognized that the number of vectors tested and the particular algorithm defining the selection and sequence of testing vectors will depend on the number of available electrodes included in a particular embodiment, their relative implant locations and the number of sensing channels available. In the embodiment shown in FIG. 2, including three anterior electrodes and one posterior electrode, all three possible anterior (A-A) vectors are tested and one anterior-posterior (A-P) vector is tested (in any order) using any of the anterior electrodes paired with the posterior electrode. It is believed that as long as any one A-P vector is acceptable and at least two of the three A-A vectors are acceptable, all the other A-P vectors will also be acceptable. This is because the three A-P vectors are essentially the same geometric vector when the three anterior electrodes are located in close proximity to each other. Two A-A vectors being acceptable suggests that all anterior electrodes incorporated on the same ICD housing are functional with good electrical contact with body fluid. The SubQ ICD will be positioned such that all anterior electrodes are making good electrical contact with the patient's tissue. As such, the remaining A-P vectors need not be tested resulting in a time savings. By reducing the number of vectors required to be tested, the overall time required to perform the selection algorithm is shortened.

It is further recognized that in alternative embodiments, only two vectors may be tested initially and if both are acceptable the two tested vectors are selected for processing for arrhythmia detection. Alternatively, all available vectors or any other subset of the available sensing vectors may be tested.

Figure 6:
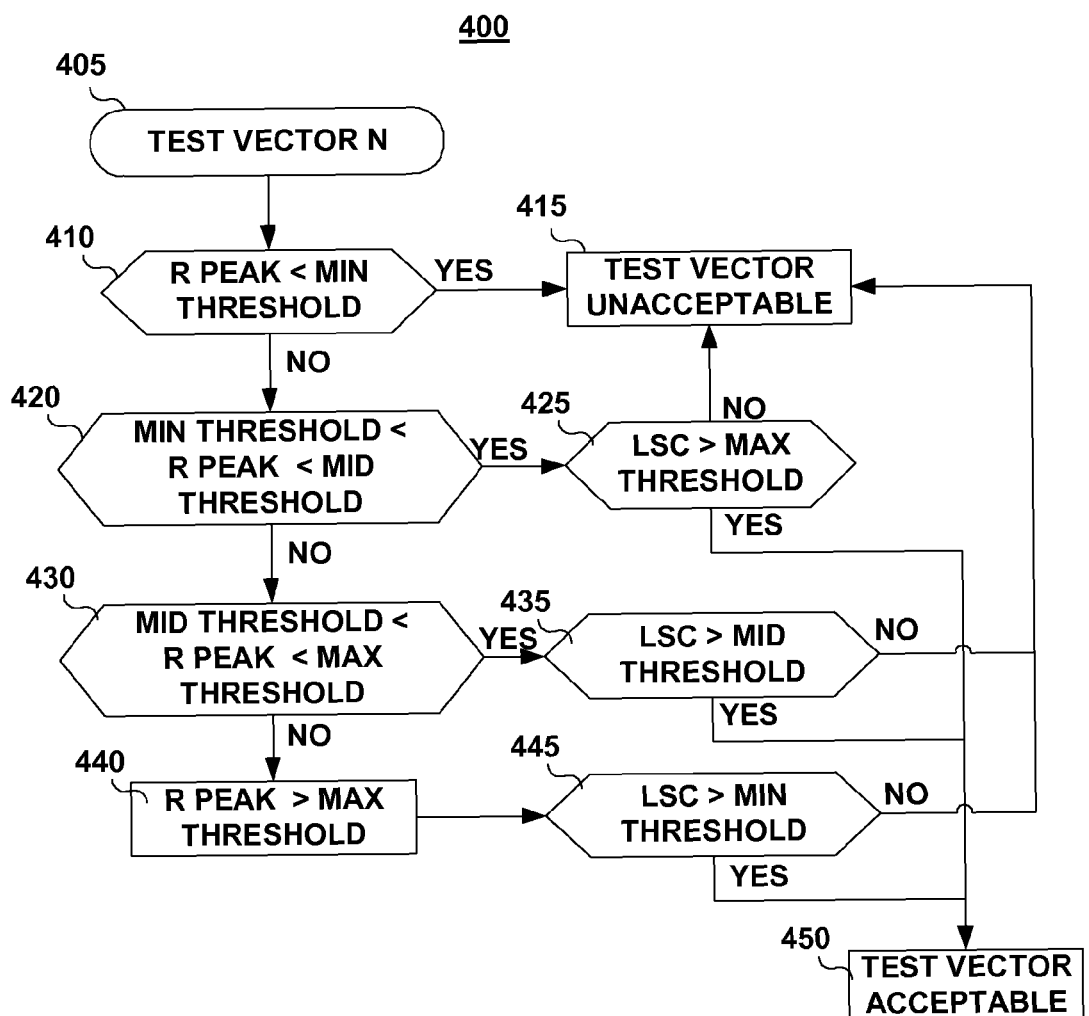
FIG. 6 is a flow chart of one method for determining the acceptability of a test sensing vector.

FIG. 6 is a flow chart of one method for determining the acceptability of a test vector. Method 400 is performed for each vector tested, or, in the alternative, for each test vector until a required number of acceptable vectors has been reached. At block 405, the signal quality parameters stored for test vector N are obtained. As described previously, a number of different signal quality parameters may be computed and stored for each test vector. In one embodiment, two signal quality parameters are computed: 1) an R-wave peak parameter computed from a defined number of measured R-wave amplitudes and 2) a low slope content (LSC) parameter computed from the low slope content for a defined number of ECG segments.

The R-wave parameter is selected for use in determining acceptability of a sensing vector to reduce the likelihood of undersensing of R-waves during tachyarrhythmias. R-wave undersensing can result in under-estimation of the actual heart rate (over-estimation of the R-R intervals due to missed R-waves). As such, it is desirable to verify that the R-wave amplitude is likely to be greater than some predetermined minimum amplitude.

The LSC parameter is selected for use in identifying acceptable sensing vectors to reduce the likelihood of false VT/VF detections. A shockable VT/VF will have a relatively low LSC. As such, the LSC during NSR should be greater than some predetermined threshold in order to reliably distinguish between shockable rhythms characterized by a low LSC and non-shockable rhythms having a relatively higher LSC.

Since the VT/VF detection algorithms used by a SubQ ICD typically rely largely on R-wave sensing for RR intervals measurements, an R-wave parameter may be given greater importance during acceptability evaluation than other parameters such as the LSC parameter. As such, the acceptability evaluation method 400 shown in FIG. 6 utilizes tiered thresholds for the R-wave parameter and for the LSC parameter. If the R-wave parameter is very high, indicating large R-wave amplitudes that will be easily sensed by the SubQ ICD sensing circuitry, the likelihood of R-wave undersensing will be relatively low, making RR interval measurements reliable for arrhythmia detection. In this case, the vector acceptability threshold for the LSC parameter can be relatively less stringent, i.e. a lower value. When the R-wave parameter is low (but still meets some absolute minimum acceptability threshold), R-wave undersensing may occur making the RR interval measurement for arrhythmia detection somewhat less reliable. The acceptability threshold for the LSC parameter threshold in this case will be more stringent, i.e. a higher value, in order to promote reliable discrimination between shockable and non-shockable rhythms.

In the embodiment shown in FIG. 6, three R-wave parameter thresholds are defined, a minimum threshold, a mid-threshold, and a maximum threshold. If the R-wave peak parameter is determined to be less than the minimum threshold, as determined at block 410, the corresponding test vector is determined to be unacceptable as indicated at block 415.

If the R-wave peak parameter is determined to be greater than the minimum threshold but less than the mid-threshold (block 420), the LSC parameter for the corresponding test vector is compared to a maximum threshold at block 425. The R-wave peak parameter that meets the minimum threshold requirement for acceptability but is relatively low requires that the LSC parameter meet a more stringent, i.e. higher, threshold for the test vector to be acceptable. If the LSC parameter is less than the maximum threshold, the vector is unacceptable (block 415). If the LSC parameter is greater than then maximum threshold, the test vector is acceptable (block 450).

If the R-wave peak parameter is greater than the mid-threshold but less than a maximum threshold (block 430), i.e. the R-wave peak parameter indicates sensing of moderate R-wave amplitudes, the LSC parameter is compared to a mid-threshold at block 435. If the LSC parameter is less than the mid-threshold, the test vector is unacceptable (block 415). If the LSC parameter is greater than the mid-threshold, the test vector is acceptable (block 450).

If the R-wave peak parameter is greater than a maximum threshold, as determined at block 440, the LSC parameter is only required to meet some minimum threshold at block 445 in order for the test vector to be identified as acceptable at block 450. If the LSC parameter does not meet the minimum threshold requirement, the test vector is determined unacceptable (block 415).

It is recognized that the actual threshold values used will depend on the particular device/electrode configuration employed (for example, the A-P thresholds may differ from the A-A thresholds), signal filter characteristics, the arrhythmia detection algorithms used by the SubQ ICD, the signal parameters and computation methods used, and may vary between individual patients. In one illustrative embodiment, the minimum, mid- and maximum R-wave peak parameter thresholds may be defined as approximately 0.2 mV, 0.3 mV, and 0.5 mV respectively. The R-wave peak parameter thresholds may range between approximately 0.05 and 0.7 mV. The minimum, mid and maximum LSC parameter thresholds may be defined as approximately 0.80, 0.60, and 0.40. The LSC parameter thresholds range from 0 to 1.

While three threshold levels or tiers are defined for each of the signal parameters, it is recognized that more or less tiers may be defined for one or both of the signal quality parameters in order to allow greater or less sensitivity to signal quality parameter differences. Decision steps may be eliminated by setting thresholds to particular values (e.g., min threshold=0 removes step 410).

Method 400 provides one illustrative embodiment wherein tiered or hierarchal acceptability thresholds are defined for a first signal quality parameter and the acceptability threshold required for a second signal quality parameter depends upon which threshold level is met by the first signal quality parameter. In other words, the threshold for the second signal quality parameter, LSC in the given example, is defined as a function of the threshold tier met by the first signal parameter, R-wave peak in this example. When a third signal quality parameter is used for determining vector acceptability, the third signal quality parameter threshold may be defined as a function of the first signal quality parameter threshold and/or the second signal quality parameter threshold and so on. In other embodiments, the LSC threshold may be defined as a mathematical function of the R-wave peak parameter value, rather than as a function of the threshold level met, wherein the mathematical function may vary depending on which threshold tier is met by the R-wave peak parameter value. In other words, the LSC threshold may be defined as LSC (threshold)=f(Rpeak) or alternatively as LSC(threshold)=f (Rpeak threshold) wherein Rpeak is the actual R-wave peak parameter value computed for the test vector and Rpeak threshold is the threshold value met by the computed R-wave peak parameter.

Figure 7:
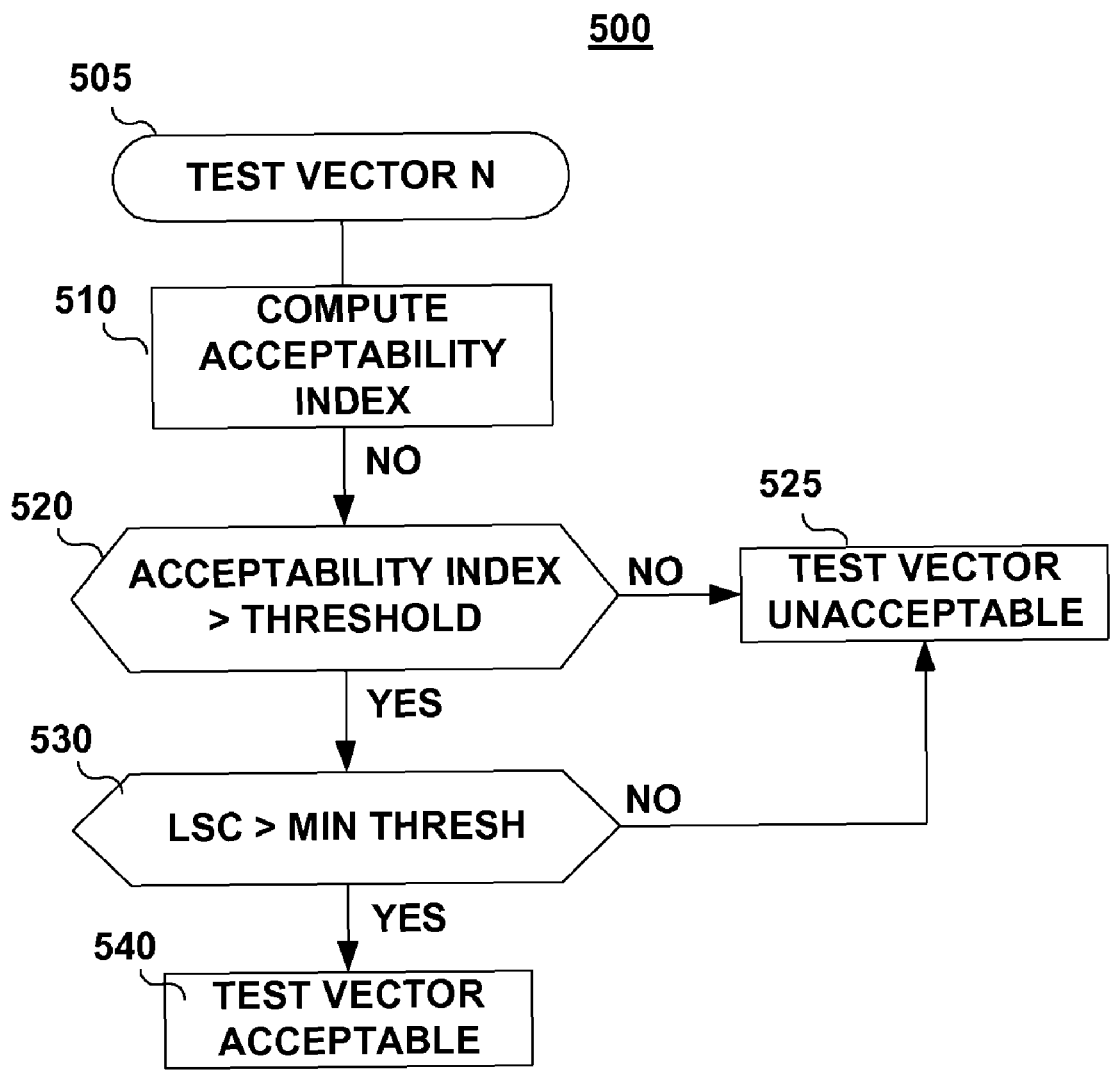
FIG. 7 is a flow chart of an alternative method for identifying acceptable sensing vectors wherein an acceptability index is defined as a function of the signal quality parameters.

FIG. 7 is a flow chart of an alternative method 500 for identifying acceptable sensing vectors wherein an acceptability index is defined as a function of the signal quality parameters. The sensitivity to small differences in the signal quality parameters will be limited by the number of threshold tiers defined in method 400. By defining an acceptability index as a function of each of the signal quality parameter values computed for a given vector greater sensitivity to small variations in the signal quality parameters can be achieved.

At block 505, a test vector is selected for evaluation. An acceptability index is computed at block 510 as a function of the signal quality parameter values computed for the test vector under evaluation. The acceptablity index is computed as a function of the signal quality parameters, which may be a weighted function, to take into account the potential trade-off between signal quality parameters that allows a lower value for one signal quality parameter to be compensated for by a higher value of another signal quality parameter. In one embodiment, the acceptability index is computed as:

$$\text{Index}=[100*\{(W1*LSC)+(W2*R\text{peak})\}]/[(W1+W2)*LSC*R\text{peak}]$$

wherein W1 and W2 are weighting factors, Rpeak is a R-wave peak amplitude parameter and LSC is a LSC parameter for a given test vector. The acceptability index is optionally normalized by dividing by the R-wave peak parameter, LSC parameter and W1 and W2 values. Multiplication by 100 is also optional and is performed merely to result in integer values for the acceptability index. The weighting factors may be optimized for a particular application to reliably distinguish between acceptable and unacceptable sensing vectors. In one example, the LSC weighting factor W1 is set equal to one and the R-wave peak weighting factor W2 is set equal to four. Any convenient linear or non-linear scaling of the parameter values may be used to adjust the parameter value ranges to approximately the same order of magnitude. Weighting and scaling factors may be selected to reduce computational complexity and simplify implementation.

The acceptability index computed at block 510 is compared to an acceptability threshold at block 520. Note that a lower index computed according to the equation provided above indicates a more acceptable vector. If the acceptability index fails to meet a threshold requirement, the test vector under question is identified as unacceptable at block 525. If the acceptability threshold requirement is met, individual threshold requirements may still be imposed on one or more of the individual signal quality parameters. For example, in one embodiment, the LSC parameter is required to be greater than a minimum threshold at block 530 in order to accept the test vector at block 540. If the LSC parameter is less than the minimum threshold, the vector may still be identified as unacceptable even though the acceptability index met a required threshold.

This additional check may be redundant depending on the weighting values used in computing the acceptability index. However, this additional requirement promotes the rejection of sensing vectors that might result in VT/VF detections based on RR intervals during high ventricular rates due to a supraventricular tachycardia. By ensuring the LSC during normal sinus rhythm is greater than some minimum threshold, the ability to distinguish between shockable and non-shockable rhythms is enhanced. It is recognized that decision block 530 is optional. Method 500 is repeated for each test vector for which signal quality parameters were measured, or until at least two, or another minimum number, of sensing vectors are identified as being acceptable.

Figure 8:
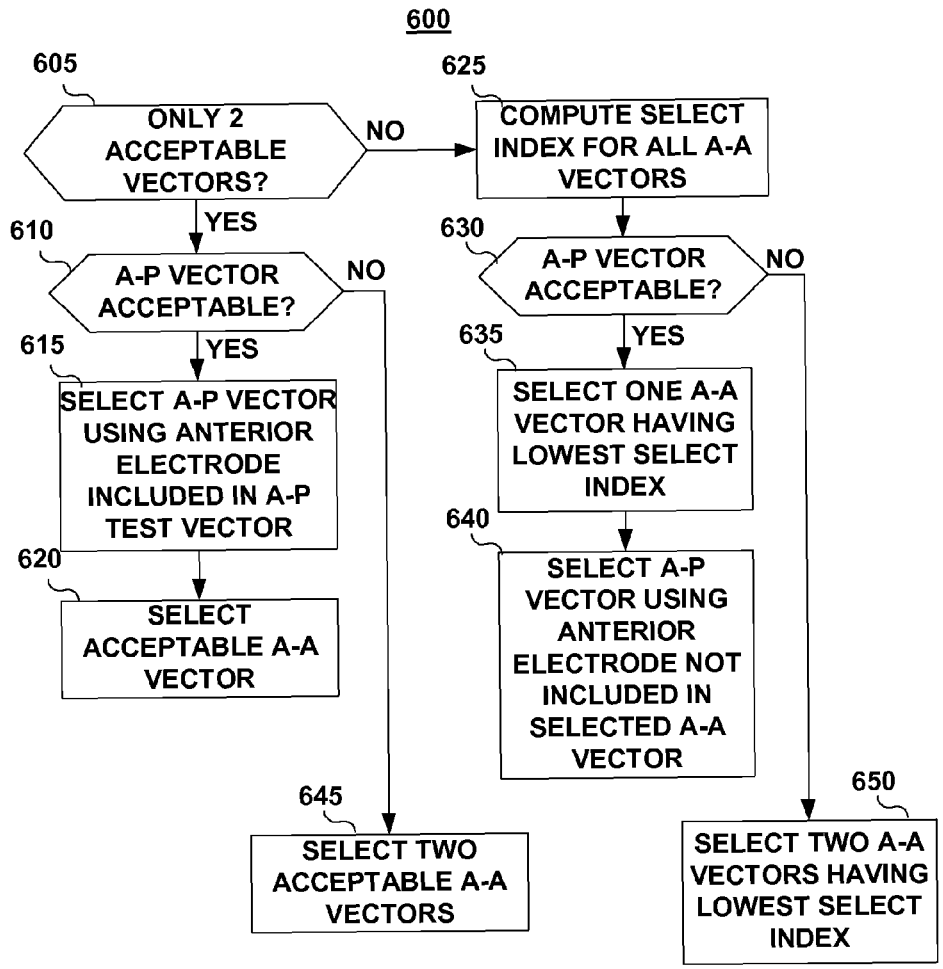
FIG. 8 is a flow chart of a method for automatically selecting sensing vectors for processing for heart rhythm monitoring.

FIG. 8 is a flow chart of a method for automatically selecting sensing vectors for processing for heart rhythm monitoring. Method 600 is performed to automatically select two of the test vectors identified as acceptable vectors for use in heart rhythm monitoring. In the illustrative embodiments described herein, it is assumed that two sensing vectors are selected for heart rhythm monitoring. However, it is recognized that in other embodiments one or three or more vectors may be selected depending on the number of available electrodes, the number of processing channels for heart rate estimation and arrhythmia detection, and the particular application. The methods described herein may easily be adapted to provide for selection of a different number of sensing vectors.

Method 600 is performed after determining which test vectors are acceptable and which test vectors are unacceptable. Only test vectors identified as acceptable, for example according to method 500 in FIG. 7, are eligible for selection. At block 605, method 600 determines if the minimum of two acceptable vectors were identified or if a greater number of acceptable vectors were identified.

If only two test vectors were identified as acceptable, method 600 determines if one of the two acceptable vectors is the A-P vector at block 610. If the A-P test vector is acceptable, that vector is selected at block 615. The A-P vector selected is the same A-P vector tested, i.e. the same anterior electrode included in the A-P test vector found to be acceptable is included in the selected A-P vector at block 615. Since only one A-A vector was found acceptable, there is uncertainty whether other untested A-P vectors would be acceptable. The remaining anterior electrode (not included in the acceptable A-A vector) may or may not be making good electrical contact with the patient's tissue. The acceptable A-A vector is then selected at block 620 as the second vector for use in heart rhythm monitoring. If the A-P test vector was not acceptable (block 610), then the two acceptable A-A vectors are selected at block 645 for processing by the SubQ ICD for heart rhythm monitoring.

If more than two test vectors were identified as acceptable (block 605), a select index may be computed for each of the acceptable A-A vectors at block 625. The select index may correspond to the acceptability index (in which case it need not be recalculated) or it may be defined as a different function of the measured signal quality parameters.

If the A-P vector is one of the acceptable vectors, as determined at block 630, an A-P vector is selected as one of the two sensing vectors. The A-P vector because of its geometrical arrangement and greater electrode separation is expected to contain more unique information when compared to a second A-A vector. For example, noise, interference or motion artifacts that affect one A-A vector will more likely affect another A-A vector to a greater degree than an A-P vector. Additionally, significantly different waveform morphology may be available on the A-P vector than on an A-A vector during VT that will aid arrhythmia classification. As such, choosing the A-P vector with one A-A vector is generally more desirable than selecting two A-A vectors. As such, if the A-P vector is acceptable, it is always selected by method 600 as one of the two sensing vectors used for heart rhythm monitoring.

If the tested A-P vector is acceptable, method 600 determines which of the acceptable A-A vectors has the most optimal select index at block 635. If the select index corresponds to the acceptability index defined above or is similarly defined, the lowest select index value corresponds to the most optimal sensing vector. As such, the acceptable A-A vector having the lowest select index is selected at block 635. The A-P vector using the remaining anterior electrode, not included in the selected A-A vector is selected as the second sensing vector at block 640 for use in heart rhythm monitoring.

An A-P vector that does not share an anterior electrode with a selected A-A vector is likely to be less sensitive to motion artifact or other interference affecting the selected A-A sensing vector. As such, it is desirable to select an A-P vector that does not share an anterior electrode with the selected A-A vector. An assumption is made that if at least two A-A vectors have been found acceptable (which will occur when more than two of the four test vectors are found acceptable as determined at block 605), then all three of the anterior electrodes will be making good electrical contact and functioning well enough to be included in the selected A-P vector.

If the A-P vector is not one of the acceptable vectors (block 630), the two A-A vectors having the lowest select index are selected at block 650 as the sensing vectors used by the SubQ ICD for heart rhythm monitoring.

Figure 9:
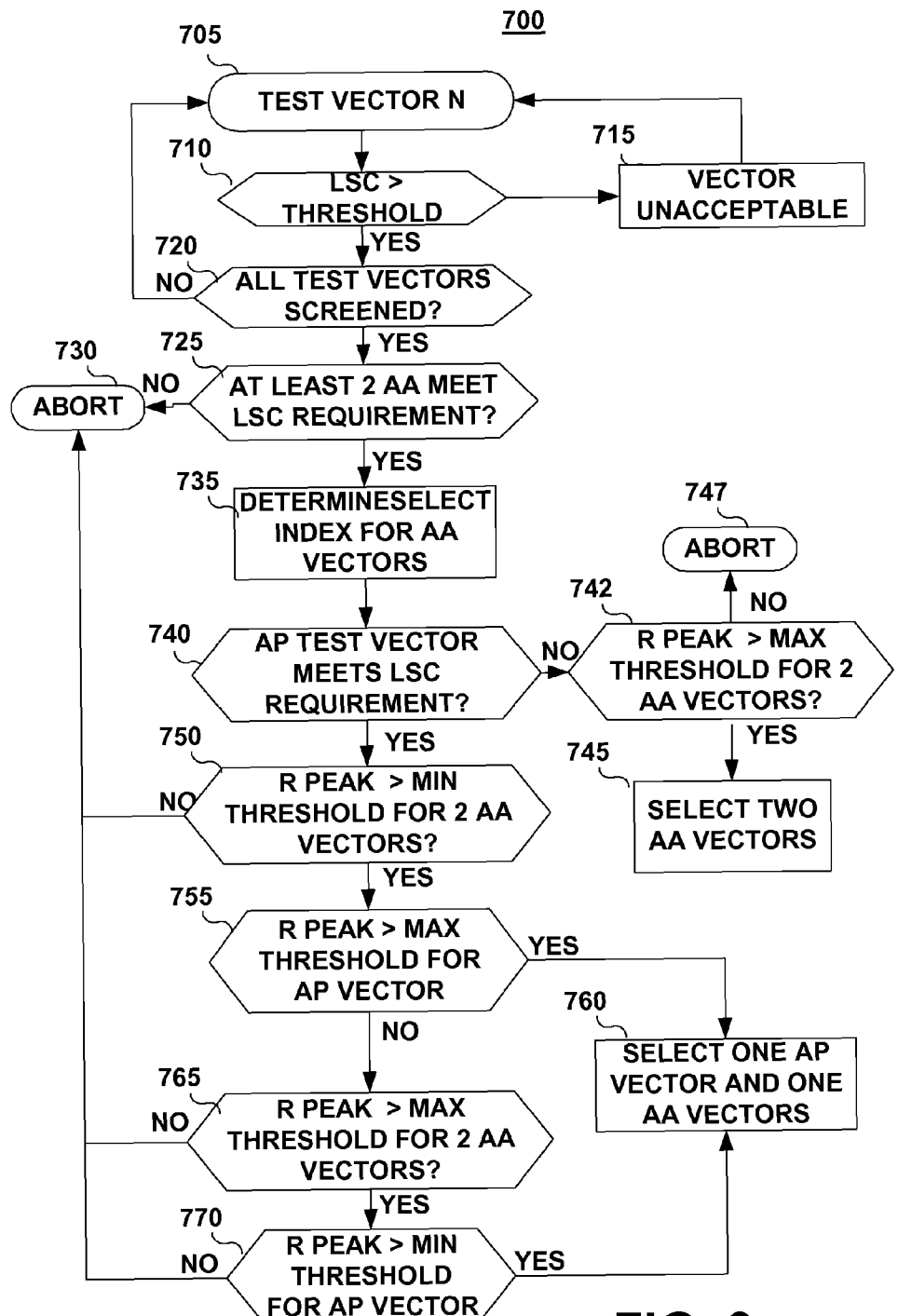
FIG. 9 is a flow chart of a method for automatically selecting sensing vectors for processing for heart rhythm monitoring according to another embodiment of the invention.

FIG. 9 is a flow chart of a method 700 for automatically selecting sensing vectors for processing for heart rhythm monitoring according to another embodiment of the invention. In the method described in conjunction with FIG. 6, tiered thresholds were described wherein, for a given sensing vector, the threshold level applied to one signal quality metric depended on the threshold level satisfied by another, different signal quality metric. In alternative embodiments, a tiered threshold scheme may be applied wherein, for a given signal quality parameter, the threshold applied to one sensing vector depends on the threshold level satisfied by another, different sensing vector.

Method 700 begins at block 705 after computing signal quality parameters for the selected subset of sensing vectors. As described previously, the signal quality parameters include an LSC metric and a R-wave peak amplitude metric.

One subset of sensing vectors includes all of the available A-A vectors and one A-P vector with respect to the embodiment shown in FIG. 2. At block 705, the signal quality parameters stored for test vector N are obtained. If the LSC parameter for any given test vector falls below a predetermined threshold, as determined at block 710, the test vector is determined as unacceptable at block 715. Otherwise, the test vector is considered acceptable and the next test vector is screened based on an LSC threshold requirement (block 720).

After screening all test vectors for acceptability, method 700 determines if at least two of the tested A-A vectors met the LSC threshold requirement at block 725. If not, method 700 is aborted at block 730. If at least two A-A test vectors are determined to be acceptable, based on the LSC threshold requirement, method 700 proceeds to determine a select index for each of the acceptable A-A vectors at block 735. The select index may be computed using the same equation defined above for the acceptability index. The select index provides an indication of the relative signal quality of the acceptable A-A vectors.

At block 740, method 700 determines if the A-P test vector met the LSC requirement for acceptability. If not, the R-wave peak amplitude metric for the least two acceptable A-A vectors is compared to a maximum threshold defined for the A-A vectors at block 742. If the R-wave peak amplitude metric meets the maximum threshold requirement at block 742 for at least two A-A vectors determined to be acceptable, then two A-A vectors are selected at block 745, from the acceptable A-A vectors meeting the maximum R-wave peak amplitude threshold. The two A-A vectors are selected as those vectors meeting both the LSC and maximum R-wave peak amplitude requirements and having the lowest or most optimal select index. If at least two acceptable A-A vectors do not meet the maximum R-wave peak threshold requirement, then the selection method 700 is aborted at block 747.

If the A-P test vector is also determined to be acceptable based on the LSC threshold requirement (block 740), the R-wave peak amplitude parameter for at least two acceptable A-A vectors is compared to a minimum threshold. If at least two of the acceptable A-A vectors do not have an R-wave peak amplitude parameter equaling or exceeding the minimum threshold, as determined at block 750, the selection method 700 is aborted at block 730. Otherwise, the R-wave peak amplitude parameter for the A-P vectors is compared to a maximum threshold at block 755. If the A-P vector is greater than the maximum R-wave peak threshold, one A-P vector and one A-A vector is selected at block 760. In other words, if the A-P vector meets some maximum R-wave threshold, two acceptable A-A vectors are only required to meet a minimum R-wave threshold defined for the A-A vectors in order to proceed with vector selection. The A-A vector is selected at block 760 as the A-A vector meeting each of the foregoing requirements (blocks 710 and 750) and having the lowest or most optimal select index. The A-P vector is selected as the A-P vector that does not include either of the anterior electrodes included in the selected A-A vector.

If the R-wave peak amplitude parameter for the A-P vector is not greater than the maximum threshold (block 755), but is greater than a minimum R-wave peak threshold (block 770), and at least two acceptable A-A vectors are greater than a maximum R-wave peak threshold defined for the A-A vectors (block 765), one A-P vector and one A-A vector is selected at block 760. In this case, if the A-P vector reaches only a minimum threshold requirement for the R-wave peak amplitude, at least two acceptable A-A vectors need to reach a maximum R-wave peak amplitude threshold in order to proceed with automatic vector selection at block 760. Vector selection made at block 760 is performed as described above.

If the A-P vector R-wave parameter is less than the minimum R-wave peak threshold (block 770) or if at least two acceptable AA vectors do not meet the maximum R-wave peak threshold defined for the AA vectors (block 770), the selection method 700 is aborted at block 730.

Generally, if the R-wave peak amplitude parameters for at least two acceptable A-A vectors do not meet a first, higher level threshold but do meet a second, lower level threshold, automatic vector selection can still be executed if the A-P vector meets a higher or more stringent threshold requirement for the R-wave peak amplitude parameter, and vice versa. In other words, for the R-wave parameter, the threshold requirement applied to the A-P vector is dependent on which threshold level or tier the acceptable A-A vectors reach, and vice versa. It is recognized that the minimum and maximum thresholds defined for the R-wave parameter, or any other given parameter, may be defined separately for the different vectors (e.g. A-A vs. A-P vectors).

Thus, an implantable medical device system and associated method for selecting subcutaneous ECG sensing electrode vectors have been presented in the foregoing description with reference to specific embodiments. It is recognized that numerous variations to the methods described herein may readily be conceived by one having skill in the art. For example, the methods described herein may be easily adapted for applications including various numbers of available subcutaneous electrodes and implant locations different than those described herein, various numbers of required sensing vectors, various numbers of sensing and processing channels, and different signal quality parameter definitions. It is appreciated that various modifications to the referenced embodiments may be made without departing from the scope of the invention as set forth in the following claims.

The invention claimed is:

1. An implantable medical device system, comprising:
    a plurality of electrodes positioned at a first subcutaneous location;
    at least one electrode positioned at a second subcutaneous location, wherein the plurality of electrodes at the first location and the electrode at the second location form multiple sensing vectors;
    a sensing module for receiving ECG signals from the multiple sensing vectors; and
    a control module configured to select a subset of the multiple sensing vectors, determine a signal quality parameter corresponding to each of the sensing vectors of the subset, determine whether each of the sensing vectors of the subset is acceptable in response to the determined signal quality parameter, and select at least one sensing vector for heart rhythm monitoring from the multiple sensing vectors in response to at least one of the subset sensing vectors being acceptable;
    wherein the subset of sensing vectors includes only one vector that includes the electrode positioned at the second location;
    wherein determining whether each of the sensing vectors of the subset is acceptable comprises comparing the signal quality parameter to a threshold requirement,
    wherein selecting at least one sensing vector for heart rhythm monitoring comprises:
        computing an acceptability index as a weighted function of a first signal quality parameter and a second signal quality parameter for each of the sensing vectors determined to be acceptable;
        comparing the computed acceptability indices; and selecting the at least one sensing vector for heart rhythm monitoring in response to the comparison of the computed acceptability indices.

2. The system of claim 1 wherein determining the signal quality parameter includes determining an R-wave peak amplitude.

3. The system of claim 1 wherein determining the signal quality parameter includes determining a low slope content.

4. The system of claim 1 wherein a first of the selected two sensing vectors is a vector including the electrode positioned at the second location and one of the plurality of electrodes positioned at the first location in response to the only one vector of the subset that includes the electrode positioned at the second location being acceptable.

5. The system of claim 4 wherein a second of the selected two sensing vectors includes two electrodes selected from the plurality of electrodes at the first location that are different electrodes than the one of the plurality of electrodes included in the first selected sensing vector.

6. The system of claim 4 wherein the first selected sensing vector is the only one vector of the subset that includes the electrode positioned at the second location in response to only two of the subset sensing vectors being acceptable.

7. The system of claim 1 wherein the first location corresponds to an anterior location.

8. The system of claim 1 wherein the second location corresponds to a posterior location.

9. The system of claim 1 further comprising a housing enclosing the sensing module and the control module, wherein the plurality of electrodes are positioned along the housing.

10. The system of claim 1, wherein determining whether each of the subset sensing vectors is acceptable further comprises
    determining a signal quality parameter of each sensing vector comprising electrodes only at the first location,
    comparing the signal quality parameter to a first threshold requirement;
    determining a second signal quality parameter of a sensing vector comprising the at least one electrode positioned at the second location, and
    comparing the second signal quality parameter to a second threshold requirement;
    wherein selecting the at least one sensing vector for heart rhythm monitoring in response to the comparison of the computed acceptability indices further comprises
    selecting the at least one vector comprising electrodes positioned only at the first location in response to the second signal quality parameter not meeting the second threshold requirement, and
    selecting one sensing vector comprising electrodes positioned only at the first location and one sensing vector comprising the at least one electrode positioned at the second location in response to the second signal quality parameter meeting the second threshold requirement.

11. The system of claim 10 wherein the first threshold requirement and the second threshold requirement are interdependent tiered thresholds.

12. A method of an implantable medical device system, comprising:
    selecting a subset of multiple sensing vectors available from a plurality of electrodes positioned at a first subcutaneous location and an electrode positioned at a second subcutaneous location wherein the subset of sensing vectors includes only one vector that includes the electrode positioned at the second location;
    determining a signal quality parameter corresponding to each of the sensing vectors of the subset,
    determining whether each of the sensing vectors of the subset is acceptable in response to the determined signal quality parameter, and selecting two sensing vectors for heart rhythm monitoring from the multiple sensing vectors in response to at least two of the subset sensing vectors being acceptable, wherein determining whether each of the sensing vectors of the subset is acceptable comprises comparing the signal quality parameter to a threshold requirement, and
    wherein selecting the two sensing vectors for heart rhythm monitoring in response to the at least two of the subset sensing vectors being acceptable comprises
        computing an acceptability index as a weighted function of a first signal quality parameter and a second signal quality parameter for each of the sensing vectors determined to be acceptable;
        comparing the computed acceptability indices; and
        selecting the two sensing vectors for heart rhythm monitoring in response to the comparison of the computed acceptability indices.

13. The method of claim 12 wherein determining the signal quality parameter includes determining an R-wave peak amplitude.

14. The method of claim 12 wherein determining the signal quality parameter includes determining a low slope content.

15. The method of claim 12 wherein selecting two sensing vectors for heart rhythm monitoring comprises selecting a first sensing vector including the electrode positioned at the second location and one of the plurality of electrodes positioned at the first location in response to the only one vector of the subset that includes the electrode positioned at the second location being acceptable.

16. The method of claim 15 wherein selecting two sensing vectors for heart rhythm monitoring comprises selecting a second sensing vector including two electrodes selected from the plurality of electrodes at the first location that are different electrodes than the one of the plurality of electrodes included in the first sensing vector.

17. The method of claim 15 wherein the first selected sensing vector is the only one vector of the subset that includes the electrode positioned at the second location in response to only two of the subset sensing vectors being acceptable.

18. The method of claim 12 wherein the first location corresponds to an anterior location.

19. The method of claim 12 wherein the second location corresponds to a posterior location.

20. The method of claim 12 wherein the plurality of electrodes is positioned along an implantable medical device housing.

21. A non-transitory computer readable medium having computer-executable instructions for performing a method comprising:
    selecting a subset of multiple sensing vectors available from a plurality of electrodes positioned at a first subcutaneous location and one electrode positioned at a second subcutaneous location wherein the subset of sensing vectors includes only one vector that includes the electrode positioned at the second location;
    determining a signal quality parameter corresponding to each of the sensing vectors of the subset,
    determining whether each of the sensing vectors of the subset is acceptable in response to the determined signal quality parameter, and selecting two sensing vectors for heart rhythm monitoring from the multiple sensing vectors in response to at least two of the subset sensing vectors being acceptable, wherein determining whether each of the sensing vectors of the subset is acceptable comprises comparing the signal quality parameter to a threshold requirement, and wherein selecting the two sensing vectors for heart rhythm monitoring in response to at least two of the subset sensing vectors being acceptable comprises:

computing an acceptability index as a weighted function of a first signal quality parameter and a second signal quality parameter for each of the sensing vectors determined to be acceptable;

comparing the computed acceptability indices; and selecting the two sensing vectors for heart rhythm monitoring in response to the comparison of the computed acceptability indices.

* * * * *